United States Patent
Tumey

(10) Patent No.: US 11,007,082 B2
(45) Date of Patent: May 18, 2021

(54) FOAM LAMINATE DRESSING

(71) Applicant: INNOVATIVE THERAPIES, INC., Pompano Beach, FL (US)

(72) Inventor: David M Tumey, Coral Springs, FL (US)

(73) Assignee: Innovative Therapies Inc., Pampano Beach, FL (US)

(*) Notice: Subject to any disclaimer, the term of this patent is extended or adjusted under 35 U.S.C. 154(b) by 168 days.

(21) Appl. No.: 14/339,057

(22) Filed: Jul. 23, 2014

(65) Prior Publication Data
US 2016/0022500 A1    Jan. 28, 2016

(51) Int. Cl.
*A61F 13/00* (2006.01)
*A61M 1/00* (2006.01)

(52) U.S. Cl.
CPC .. *A61F 13/00068* (2013.01); *A61F 13/00008* (2013.01); *A61F 13/00029* (2013.01); *A61M 1/0088* (2013.01); *A61F 2013/00319* (2013.01); *A61F 2013/00323* (2013.01)

(58) Field of Classification Search
CPC .......... A61F 13/00068; A61F 13/00008; A61F 13/00029; A61F 2013/00319; A61F 2013/00323; A61M 1/0088
USPC ....................................................... 604/307
See application file for complete search history.

(56) References Cited

U.S. PATENT DOCUMENTS

| | | |
|---|---|---|
| 2,232,254 A | 2/1941 | Morgan |
| 2,338,339 A | 1/1944 | LeMere et al. |
| 2,547,758 A | 4/1951 | Keeling |
| 2,969,057 A | 1/1961 | Simmons |
| 3,026,526 A | 3/1962 | Montrose |
| 3,026,874 A | 3/1962 | Stevens |
| 3,367,332 A | 2/1968 | Groves |
| 3,478,736 A | 11/1969 | Roberts et al. |
| 3,481,326 A | 12/1969 | Schamblin |
| 3,486,504 A | 12/1969 | Austin, Jr. |
| 3,610,238 A | 10/1971 | Rich, Jr. |
| 3,682,180 A | 8/1972 | McFarlane |
| 3,826,254 A | 7/1974 | Mellor |
| 3,874,387 A | 4/1975 | Barbieri |
| 3,896,810 A | 7/1975 | Akiyama |
| 3,908,664 A | 9/1975 | Loseff |
| 3,954,105 A | 5/1976 | Nordby et al. |
| 3,993,080 A | 11/1976 | Loseff |

(Continued)

FOREIGN PATENT DOCUMENTS

| | | |
|---|---|---|
| CN | 1206340 A | 1/1999 |
| CN | 1211911 A | 3/1999 |

(Continued)

OTHER PUBLICATIONS

Ebnesajjad, Sina, editor. "Chapter 1—Introduction and Adhesion Theories." Adhesives Technology Handbook, 2nd ed., William Andrew Applied Science Publishers, 2009, pp. 1-19 (Year: 2009).*

(Continued)

*Primary Examiner* — Andrew J Mensh
(74) *Attorney, Agent, or Firm* — Arent Fox LLP

(57) ABSTRACT

A foam laminate dressing includes a first distinct hydrophobic reticulated foam layer and an underlying second distinct hydrophilic layer bonded to the first layer and of substantially same length and width as the first distinct hydrophobic reticulated foam layer.

10 Claims, 3 Drawing Sheets

(56) References Cited

U.S. PATENT DOCUMENTS

| | | | |
|---|---|---|---|
| 4,000,028 A * | 12/1976 | Hoey | A61F 13/00008 |
| | | | 156/79 |
| RE29,319 E | 7/1977 | Nordby et al. | |
| 4,080,970 A | 3/1978 | Miller | |
| 4,112,947 A | 9/1978 | Nehring | |
| 4,149,541 A | 4/1979 | Gammons et al. | |
| 4,169,563 A | 10/1979 | Leu | |
| 4,172,455 A | 10/1979 | Beaussant | |
| 4,224,945 A | 9/1980 | Cohen | |
| 4,250,882 A | 2/1981 | Adair | |
| 4,256,109 A | 3/1981 | Nichols | |
| 4,261,363 A | 4/1981 | Russo | |
| 4,275,721 A | 6/1981 | Olson | |
| 4,297,995 A | 11/1981 | Golub | |
| 4,373,519 A | 2/1983 | Errede et al. | |
| 4,382,441 A | 5/1983 | Svedman | |
| 4,392,853 A | 7/1983 | Muto | |
| 4,419,097 A | 12/1983 | Rowland | |
| 4,441,357 A | 4/1984 | Kahn et al. | |
| 4,443,511 A * | 4/1984 | Worden | B32B 38/0012 |
| | | | 428/198 |
| 4,469,092 A | 9/1984 | Marshall et al. | |
| 4,475,909 A | 10/1984 | Eisenberg | |
| 4,480,638 A | 11/1984 | Schmid | |
| 4,525,166 A | 6/1985 | Leclerc | |
| 4,527,064 A | 7/1985 | Anderson | |
| 4,540,412 A | 9/1985 | Van Overloop | |
| 4,543,100 A | 9/1985 | Brodsky | |
| 4,569,674 A | 2/1986 | Phillips et al. | |
| 4,573,965 A | 3/1986 | Russo | |
| 4,605,399 A | 8/1986 | Weston et al. | |
| 4,608,041 A | 8/1986 | Neilsen | |
| 4,624,656 A | 11/1986 | Clark et al. | |
| 4,640,688 A | 2/1987 | Hauser | |
| 4,661,093 A | 4/1987 | Beck et al. | |
| 4,710,165 A | 12/1987 | McNeil et al. | |
| 4,713,052 A | 12/1987 | Beck | |
| 4,743,232 A | 5/1988 | Kruger | |
| 4,755,168 A | 7/1988 | Romanelli et al. | |
| 4,759,354 A | 7/1988 | Quarfoot | |
| 4,764,167 A | 8/1988 | Tu | |
| 4,765,316 A | 8/1988 | Marshall | |
| 4,778,456 A | 10/1988 | Lokken | |
| 4,820,265 A | 4/1989 | DeSatnick et al. | |
| 4,820,284 A | 4/1989 | Hauri | |
| 4,834,110 A | 5/1989 | Richard | |
| 4,836,192 A | 6/1989 | Abbate | |
| 4,838,883 A | 6/1989 | Matsuura | |
| 4,840,187 A | 6/1989 | Brazier | |
| 4,851,545 A | 7/1989 | Song et al. | |
| 4,863,449 A | 9/1989 | Therriault et al. | |
| 4,878,901 A | 11/1989 | Sachse | |
| 4,906,233 A | 3/1990 | Moriuchi et al. | |
| 4,917,112 A | 4/1990 | Kalt | |
| 4,921,492 A | 5/1990 | Schultz et al. | |
| 4,925,447 A | 5/1990 | Rosenblatt | |
| 4,931,519 A | 6/1990 | Song et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,969,881 A | 11/1990 | Viesturs | |
| 5,035,884 A | 7/1991 | Song et al. | |
| 5,086,764 A | 2/1992 | Gilman | |
| 5,100,396 A | 3/1992 | Zamierowski | |
| 5,106,362 A | 4/1992 | Gilman | |
| 5,113,871 A | 5/1992 | Viljanto et al. | |
| 5,149,331 A | 9/1992 | Ferdman et al. | |
| 5,176,663 A | 1/1993 | Svedman | |
| 5,228,431 A | 7/1993 | Giarretto | |
| 5,261,893 A | 11/1993 | Zamierowski | |
| 5,358,494 A | 10/1994 | Svedman | |
| 5,527,293 A | 6/1996 | Zamierowski | |
| 5,636,643 A | 6/1997 | Argenta et al. | |
| 5,645,081 A | 7/1997 | Argenta et al. | |
| 5,779,657 A | 7/1998 | Daneshvar | |
| 6,071,267 A | 6/2000 | Zamierowski | |
| 6,087,549 A | 7/2000 | Flick | |
| 6,135,116 A | 10/2000 | Vogel | |
| 6,142,982 A | 11/2000 | Hunt et al. | |
| 6,196,992 B1 | 3/2001 | Keilman et al. | |
| 6,398,767 B1 | 6/2002 | Fleischmann | |
| 6,432,438 B1 | 8/2002 | Shukla | |
| 6,458,109 B1 | 10/2002 | Henley et al. | |
| 6,345,623 B1 | 12/2002 | Heaton et al. | |
| 6,551,280 B1 | 4/2003 | Knighton et al. | |
| 6,553,998 B2 | 4/2003 | Heaton et al. | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,755,807 B2 | 6/2004 | Risk et al. | |
| 6,800,074 B2 | 10/2004 | Henley et al. | |
| 6,814,079 B2 | 11/2004 | Heaton et al. | |
| 6,840,960 B2 | 1/2005 | Bubb | |
| 6,841,715 B2 | 1/2005 | Roberts | |
| 6,855,135 B2 | 2/2005 | Lockwood et al. | |
| 6,856,821 B2 | 2/2005 | Johnson | |
| 6,979,324 B2 | 12/2005 | Bybordi et al. | |
| 7,004,915 B2 | 2/2006 | Boynton et al. | |
| 7,022,113 B2 | 4/2006 | Lockwood et al. | |
| 7,070,584 B2 | 7/2006 | Johnson et al. | |
| 7,108,683 B2 * | 9/2006 | Zamierowski | A61M 1/0058 |
| | | | 604/304 |
| 7,117,869 B2 | 10/2006 | Heaton et al. | |
| 7,144,390 B1 | 12/2006 | Hannigan et al. | |
| 7,195,624 B2 | 3/2007 | Lockwood et al. | |
| 7,198,046 B1 | 4/2007 | Argenta et al. | |
| 7,214,202 B1 | 5/2007 | Vogel | |
| 7,216,651 B2 | 5/2007 | Argenta et al. | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| 7,338,482 B2 | 3/2008 | Lockwood et al. | |
| 7,361,184 B2 | 4/2008 | Joshi | |
| 7,381,859 B2 | 6/2008 | Hunt et al. | |
| 7,422,576 B2 | 9/2008 | Boynton et al. | |
| 7,438,705 B2 | 10/2008 | Karpowicz et al. | |
| 7,520,872 B2 | 4/2009 | Biggie et al. | |
| 7,524,286 B2 | 4/2009 | Johnson | |
| 7,524,315 B2 | 4/2009 | Blott et al. | |
| 7,532,953 B2 | 5/2009 | Vogel | |
| 7,534,240 B1 | 5/2009 | Johnson | |
| 7,534,927 B2 | 5/2009 | Lockwood et al. | |
| 7,540,848 B2 | 6/2009 | Hannigan et al. | |
| 7,553,306 B1 | 6/2009 | Hunt et al. | |
| 2001/0031943 A1 | 10/2001 | Urie | |
| 2002/0065494 A1 | 5/2002 | Lockwood et al. | |
| 2003/0078532 A1 * | 4/2003 | Ruszczak | A61L 15/225 |
| | | | 602/46 |
| 2003/0225355 A1 | 12/2003 | Butler | |
| 2004/0002670 A1 | 1/2004 | Mothersbaugh et al. | |
| 2004/0219133 A1 | 11/2004 | Lyles | |
| 2005/0095723 A1 | 5/2005 | DiTrolio et al. | |
| 2005/0137539 A1 | 6/2005 | Biggie et al. | |
| 2005/0203469 A1 | 9/2005 | Bobroff et al. | |
| 2005/0209574 A1 | 9/2005 | Boehringer et al. | |
| 2005/0228329 A1 | 10/2005 | Boehringer et al. | |
| 2005/0245904 A1 | 11/2005 | Estes et al. | |
| 2006/0025727 A1 | 2/2006 | Boehringer et al. | |
| 2006/0100586 A1 | 5/2006 | Karpowicz et al. | |
| 2007/0027414 A1 | 2/2007 | Hoffman et al. | |
| 2007/0032762 A1 | 2/2007 | Vogel | |
| 2007/0032763 A1 | 2/2007 | Vogel | |
| 2007/0219532 A1 | 9/2007 | Karpowicz et al. | |
| 2009/0227969 A1 | 9/2009 | Jaeb et al. | |
| 2010/0298791 A1 * | 11/2010 | Jones | A61F 13/00012 |
| | | | 604/319 |
| 2010/0305490 A1 * | 12/2010 | Coulthard | A61M 1/0088 |
| | | | 602/43 |
| 2011/0178451 A1 | 7/2011 | Robinson et al. | |

(56) References Cited

U.S. PATENT DOCUMENTS

| | | |
|---|---|---|
| 2011/0213287 A1 | 9/2011 | Lattimore et al. |
| 2012/0036733 A1* | 2/2012 | Dehn ................ A61F 13/00008 34/282 |
| 2012/0143113 A1 | 6/2012 | Robinson et al. |

FOREIGN PATENT DOCUMENTS

| | | |
|---|---|---|
| CN | 1354648 A | 6/2002 |
| CN | 1400268 A | 3/2003 |
| CN | 1449305 A | 10/2003 |
| CN | 102844176 A | 12/2012 |
| DE | 28 09-828 | 9/1978 |
| DE | 41 11 122 | 4/1993 |
| DK | 64055 | 10/1945 |
| EP | 0 880 953 | 12/1998 |
| GB | 641061 | 8/1950 |
| GB | 1273342 | 5/1972 |
| SU | 0587941 | 1/1978 |
| SU | 1268175 | 11/1986 |
| WO | 8001139 | 6/1980 |
| WO | 8905133 | 6/1989 |
| WO | WO-90/11795 | 10/1990 |
| WO | 9100718 | 1/1991 |
| WO | WO-91/16030 | 10/1991 |
| WO | WO-92/19313 | 11/1992 |
| WO | WO-92/20299 | 11/1992 |
| WO | WO-96/05873 | 2/1996 |
| WO | WO/01/30422 | 5/2001 |
| WO | 2010092334 A1 | 8/2010 |
| WO | 2010097570 A1 | 9/2010 |
| WO | 2012118975 A2 | 9/2012 |

OTHER PUBLICATIONS

Chinn, Steven D et al., "Closed Wound Suction Drainage", The Journal of Foot Surgery, vol. 24, No. 1, 1985, pp. 76-81.
Wooding-Scott, Margaret et al., "No Wound is Too Big for Resourceful Nurses", RN, Dec. 1988, pp. 22-25.
P. Svedman, M.D., "A Dressing System Providing Fluid Supply and Suction Drainage Used for Continuous or Intermittent Irrigation", Annals of Plastic Surgery, vol. 17, No. 2, Aug. 1986, pp. 125-133.
Arnljots, Bjorn, et al. "Irrigation Treatment in Split-Thickness Skin Grafting of Intractable Leg Ulcers", Scand J Plast Reconstr Surg 19: 211-213, 1985.
Teder, H. et al., "Continuous Wound Irrigation in the Pig", Journal of Investigative Surgery, vol. 3, pp. 399-407, 1990.
Chariker M.D., Mark E., "Effective Management of Incisional and Cutaneous Fistulae with Closed Suction Wound Drainage", Contemporary Surgery, vol. 34, Jun. 1989, pp. 59-63.
Mizuno M.D., Katsuyoshi, "Suctioning Sponge", Arch Ophthalmol, vol. 101, Feb. 1983, p. 294.
Nicolov, An., "A Method of Treatment of Postphlebitic and Varicose Trophyc Ulcers of the Lower Extremities by Vacuum", 6 pages, Translation from Bulgarian into English, 1979, Surgery, XXXIV, 1981, Apr. 4, 1979.
Smith, S.R.G., et al., "Surgical Drainage", Surgical Symposium, British Journal of Hospital Medicine, Jun. 1985, pp. 308, 311, 314-315.
Westaby, S. et al., "Treatment of Purulent Wounds and Fistulae with an Adhesive Wound Irrigation Device", Instruments and Techniques, Annals of the Royal College of Surgeons of England (1981), vol. 63, pp. 353-356.
Borzov, M.V., et al., "The Vacuum Therapy of Some Skin Conditions", The Odessa N.I. Pirogov Medical Institute, Submitted, Apr. 9, 1965.
Svedman P., "Irrigation Treatment of Leg Ulcers", The Lancet, Sep. 3, 1983, pp. 532-534.
International Preliminary Report on Patentability for Application No. PCT/US2015/041502, dated Jan. 24, 2017, 6 pages.
International Search Report and Written Opinion for Application No. PCT/U52015/041502, dated Sep. 17, 2015, 11 pages.
Office Action for Colombian Application No. NC2017/0001409, 5 pages.

* cited by examiner

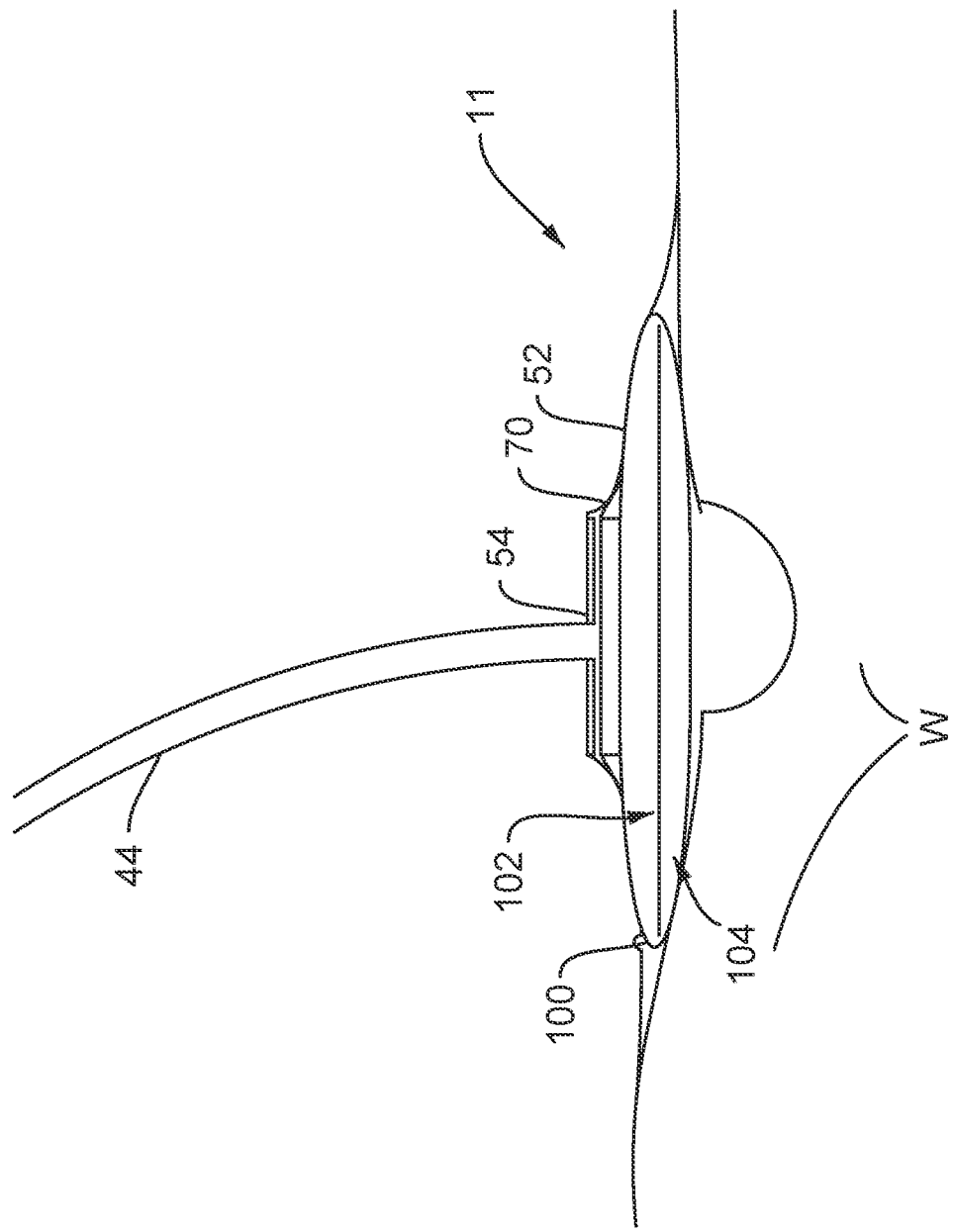

FOAM LAMINATE DRESSING

FIELD OF INVENTION

The invention relates to wound dressings. More particularly, the invention is directed to wound dressings which are used in conjunction with a negative pressure wound therapy device.

PRIOR ART

In the field of wound dressings, there exist many different types of materials which are used for various applications. In the case of negative pressure wound dressings, typically a foam material is employed through which wound exudate and/or cleansing fluids can pass.

Hydrophilic polyurethanes are a hydrophilic and are compatible with water in controlled delivery devices, such as wound care dressings. Hydrophilic polyurethanes are conventionally made by the emulsification and curing of an aqueous phase with a hydrophilic polyurethane prepolymer. The aqueous phase may contain an active ingredient in which case the ingredient is dispersed in the matrix of the resultant foam.

A variation in the foam is known as reticulated foam. These foams are constructed such that relatively large openings exist in individual cells making up the foam structure and provide for flow of air or water therethrough. It is often used as a filter media due to their typically low density and corresponding low cost per unit volume. These foams are hydrophobic, i.e. they do not absorb water.

Hydrophilic polyurethanes can be formulated with active ingredients which is not the case with conventional reticulated polyurethanes. Hydrophilic polyurethane is compatible with and absorbs water while the conventional polyurethanes are hydrophobic and are incompatible with water. Hydrophilic polyurethane is useful in its absorptive ability, it typically has poor physical strength and relatively high densities causing a relatively high cost per unit volume.

One prior use in the field was directed to forming a dressing by coating an inside surface of the open cell reticulated foam with a polyurethane prepolymer emulsion and allowing the composite to cure. The result is a foam composite that uses the open cell polyurethane foam as a scaffold or a substrate on which the hydrophilic polyurethane foam is cast. The prior art provides a composite which includes a hydrophobic scaffold foam, such as an open cell or open cell reticulated polyurethane foam, coated with an open cell hydrophilic polyurethane foam. This is accomplished by coating the inside surface of the open cell foam with a polyurethane prepolymer emulsion and allowing the composite to cure. What results is a foam composite that uses the open cell polyurethane foam as a scaffold or a substrate on which the hydrophilic polyurethane foam is cast.

While these types of dressings have been useful in certain applications, there remains a need for improvement in the field of wound dressings.

SUMMARY OF THE INVENTION

It is an object of the present invention to provide improved foam laminate.

It is another object to improve wound dressings by providing a laminate with a distinct hydrophobic foam layer and a distinct hydrophilic foam layer.

It is another object of the present invention to provide foam laminate which can be used as a dressing through which a fluid stream passes in association with a negative pressure device.

Accordingly, the present invention is directed to a foam laminate which includes a first distinct hydrophobic reticulated foam layer and a second distinct hydrophilic layer bonded to the first layer. The layers can be bonded by heat, adhesive, or during a formation process where the two layers are immediately disposed one another such that part of the facing surfaces mechanically interlock upon curing. Polyurethanes can be used to form both hydrophobic and hydrophilic foam layers. In a preferred embodiment, the formed laminate is spiral cut with perforations to enable the laminate to be easily torn to accommodate a particular wound size.

By combining these two types of foam layers, the resulting laminate provides an excellent advantage over prior art devices which provides for the excellent absorptive features of the hydrophilic layer in the treatment of the wound, while the reticulated hydrophobic layer is disposed adjacent a hermetic sealing layer that surrounds the dressing and seals to the skin about the wound. The sealing layer typically includes a port connected to a negative pressure device. The reticulated hydrophobic layer enables an even distribution of vacuum over the dressing which promotes superior wound healing.

These and other features, aspects, and advantages of the present invention will be readily apparent to those of ordinary skill in the art when read in conjunction with the following description, appended claims and accompanying drawings.

BRIEF DESCRIPTION OF THE DRAWINGS

FIG. 4 is a schematic of one embodiment of the invention.

DESCRIPTION OF THE PREFERRED EMBODIMENTS

Figure 1:
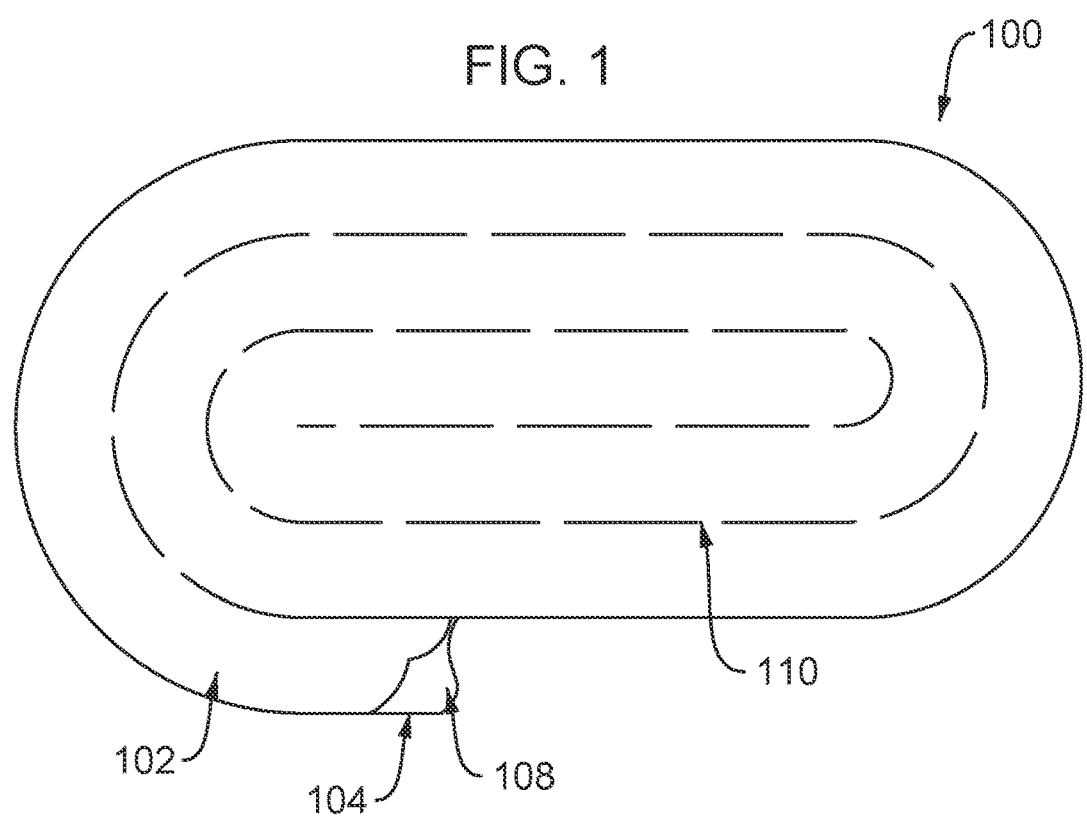
FIG. 1 is a schematic view of the foam laminate dressing of the present invention.
Figure 2:
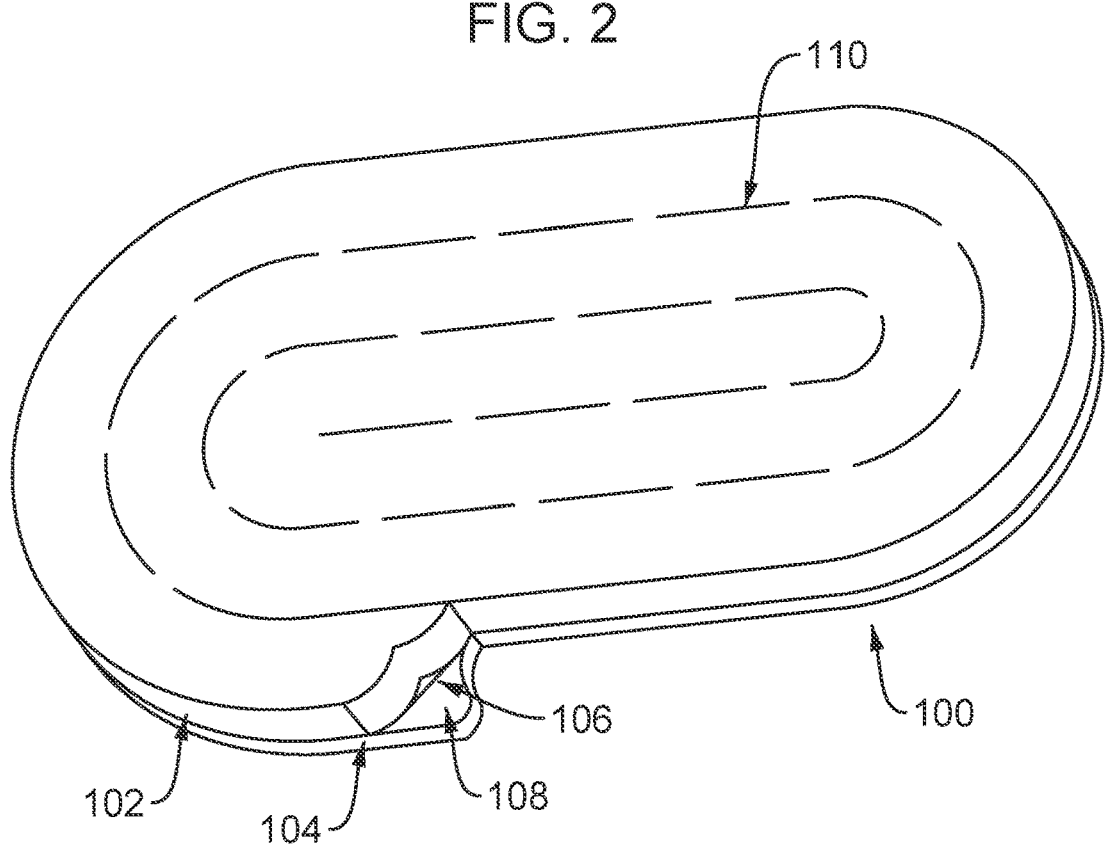
FIG. 2 is a perspective view of the foam laminate dressing of FIG. 1.

In the following description of preferred embodiments of the invention, reference is made to the accompanying figures of the drawing which form a part hereof, and in which are shown, by way of illustration, specific embodiments in which the invention may be practiced. It is to be understood that other embodiments may be used and structural changes may be made without departing from the scope of the present invention.

The foam laminate dressing of the present invention is generally designated by the numeral 100 promotes healing of a wound via the use of a pump system. Negative pressure wound therapy (NPWT), also known as vacuum drainage or closed-suction drainage, can be employed as part of the instant invention.

The foam laminate 100 includes a first distinct hydrophobic reticulated foam layer 102 and a second distinct hydrophilic layer 104 bonded to the first layer 102. The layers 102 and 104 can be bonded by heat, adhesive, or during a formation process where the two layers 102 and 104 are immediately disposed one another such that part of the facing surfaces 106 and 108, respectively, mechanically interlock upon curing. Polyurethanes can be used to form both hydrophobic and hydrophilic foam layers 102 and 104. In a preferred embodiment, the formed laminate 100 can be spiral cut with perforations 110 to enable the laminate to be easily torn to accommodate a particular wound size.

By combining these two types of foam layers, the resulting laminate 100 provides an excellent advantage over prior art devices which provides for the excellent absorptive features of the hydrophilic layer 104 in the treatment of the wound, while the reticulated hydrophobic layer is disposed adjacent a hermetic sealing layer 52 which surrounds the foam laminate dressing 100 and seals to the skin about the wound W. The sealing layer typically includes a port 54 connected to a negative pressure device 10. The reticulated hydrophobic layer 102 enables an even distribution of vacuum over the dressing 100 which promotes superior wound healing.

In a preferred application of the invention, a therapeutic device of the instant invention is generally designated by the numeral 10. The therapeutic device 10 can preferably include a housing 12 which can preferably be formed in a waterproof manner to protect components therein. In this regard, housing 12 can have a watertight sealed access panel 13 through which components can be accessed.

The device 10 can include a processor 14, which can be a microcontroller having an embedded microprocessor, Random Access Memory (RAM) and Flash Memory (FM). FM can preferably contain the programming instructions for a control algorithm. FM can preferably be non-volatile and retains its programming when the power is terminated. RAM can be utilized by the control algorithm for storing variables such as pressure measurements, alarm counts and the like, which the control algorithm uses while generating and maintaining the vacuum.

A membrane keypad and a light emitting diode LED or liquid crystal display (LCD) 16 can be electrically associated with processor 14 through a communication link, such as a cable. Keypad switches provide power control and are used to preset the desired pressure/vacuum levels. Light emitting diodes 17, 19 can be provided to indicate alarm conditions associated with canister fluid level, leaks of pressure in the dressing and canister, and power remaining in the power source.

Microcontroller 14 is electrically associated with, and controls the operation of, a first vacuum pump 18 and an optional second vacuum pump 20 through electrical connections. First vacuum pump 18 and optional second vacuum pump 20 can be one of many types including, for example, the pumps sold under the trademarks Parker Precision Fluidics® and Thomas®. Vacuum pumps 18 and 20 can use, for example, a reciprocating diaphragm or piston to create vacuum and can be typically powered by a direct current (DC) motor that can also optionally use a brushless commutator for increased reliability and longevity. Vacuum pumps 18 and 20 can be pneumatically associated with a disposable exudate collection canister 22 through a single-lumen tube 24.

In one embodiment, canister 22 has a volume which does not exceed 1000 ml. This can prevent accidental exsanguination of a patient in the event hemostasis has not yet been achieved at the wound site. Canister 22 can be of a custom design or one available off-the-shelf and sold under the trademark DeRoyal®.

Figure 3:
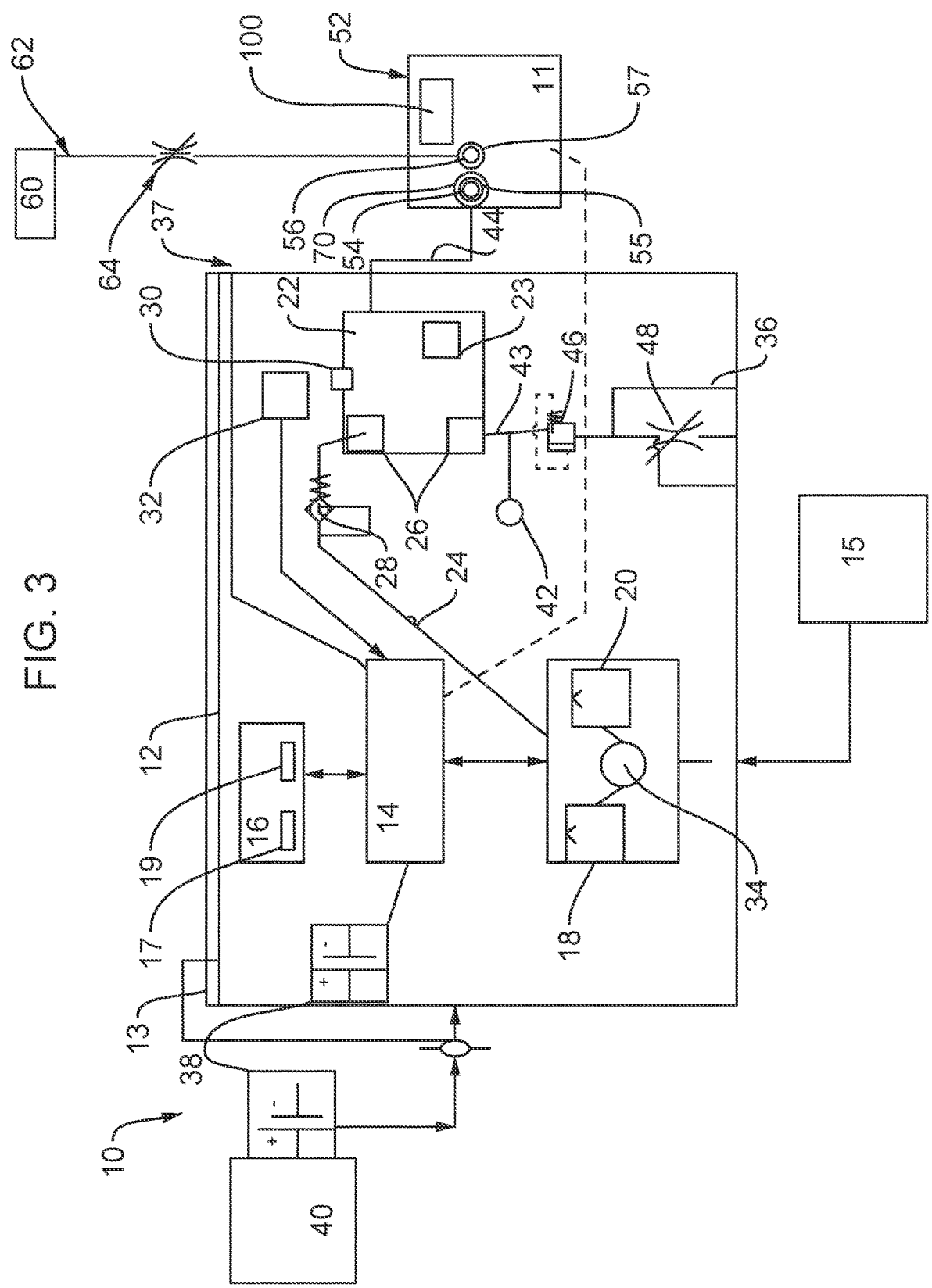
FIG. 3 depicts a sectional view of the foam laminate dressing in FIG. 1 as part of a negative pressure wound therapy system.

Referring to FIG. 3, a fluid barrier 26, which can be a back flow valve or filter, is associated with canister 22 and is configured to prevent fluids collected in canister 22 from escaping into tubing 24 and fouling the vacuum return path. Barrier 26 can be of a mechanical float design or may have one or more membranes of hydrophobic material such as those available under the trademark GoreTex™. Barrier 26 can also be fabricated from a hydrophobic porous polymer such as that which is available under the trademark MicroPore™. A secondary barrier 28 using a hydrophobic membrane or valve is inserted in-line with pneumatic tubing 24 to prevent fluid ingress into the system in the event barrier 26 fails to operate as intended. Pneumatic tubing 24 can connect to first vacuum pump 18 and optional second vacuum pump 20 through "T" connectors.

An identification member 30, such as radio frequency identification (RFID) tag, can be physically associated with the canister 22 and an RFID sensor 32 operably associated with the microcontroller 14 such that the microcontroller 14 can restrict use of the device 10 to a predetermined canister 22. Thus, if a canister 22 does not have a predetermined RFID chip, the device 10 will not operate. Another embodiment envisions software resident on microcontroller 14 which restricts the use of the device 10 to a predetermined time period such as 90 days for example. In this way, the patient using the device 10 may use the device 10 for a prescribed time period and then the device 10 automatically times out per a particular therapeutic plan for that patient. This also enables a reminder of the time and date for the next dressing change or physician appointment. It is also contemplated that the microcontroller 14 be operably provided with a remote control 15 and communication link, such as a transceiver, wherein the device 10 can be shut down remotely when a particular therapeutic plan for that patient has ended. Likewise, remote control 15 can be utilized to provide additional time after the therapeutic device times out.

Vacuum-pressure sensor 34 is pneumatically associated with first vacuum pump 18 and optional vacuum pump 20 and electrically associated with microcontroller 14. Pressure sensor 34 provides a vacuum-pressure signal to the microprocessor enabling a control algorithm to monitor vacuum pressure at the outlet of the vacuum pumps 18 and 20.

An acoustic muffler can be provided and pneumatically associated with the exhaust ports of vacuum pumps 18 and 20 and configured to reduce exhaust noise produced by the pumps during operation. In normal operation of device 10, first vacuum pump 18 can be used to generate the initial or "draw-down" vacuum while optional second vacuum pump 20 can be used to maintain a desired vacuum within the system compensating for any leaks or pressure fluctuations. Vacuum pump 20 can be smaller and quieter than vacuum pump 18 providing a means to maintain desired pressure without disturbing the patient. A switch 37 can be operatively disposed on housing 12 in operable connection with microcontroller 14 to enable selection of positive and negative pressure from pumps 18/20.

One or more battery (ies) 38 can preferably be provided to permit portable operation of the device 10. Battery 38 can be Lithium Ion (LiIon), Nickel-Metal-Hydride (NiMH), Nickel-Cadmium, (NiCd) or their equivalent, and can be electrically associated with microcontroller 14 through electrical connections. Battery 38 can be of a rechargeable type which is preferably removably disposed in connection with the housing 12 and can be replaced with a secondary battery 38 when needed. A recharger 40 is provided to keep one battery 38 charged at all times. Additionally, it is contemplated that the device 10 can be equipped to be powered or charged by recharger 40 or by circuits related with microcontroller 14 if such source of power is available. When an external source of power is not available and the device 10 is to operate in a portable mode, battery 38 supplies power to the device 10. The battery 38 can be rechargeable or reprocessable and can preferably be removably stored in a waterproof manner within housing 12 which also likewise contains the pumps 18, 20 and microcontroller 14.

A second pressure sensor 42 is pneumatically associated with canister 22 through a sensor port 43. Pressure sensor 42 can be electrically associated with microcontroller 14 and provides a vacuum-pressure signal to microprocessor enabling control algorithm to monitor vacuum pressure inside canister 22 and dressing 11. A "T" connector can be connected to port 43, to pressure sensor 42 and a vacuum-pressure relief solenoid 46 configured to relieve pressure in the canister 22 and dressing 11 in the event of an alarm condition, or if power is turned off. Solenoid 46, can be, for example, one available under the trademark Parker Hannifin® or Pneutronics®; Solenoid 46 is electrically associated with, and controlled by, microprocessor of microcontroller 14. Solenoid 46 can be configured to vent vacuum pressure to atmosphere when an electrical coil associated therewith is de-energized as would be the case if the power is turned off. An orifice restrictor 48 may optionally be provided in-line with solenoid 46 and pneumatic tube 44 to regulate the rate at which vacuum is relieved to atmospheric pressure when solenoid 46 is de-energized. Orifice restrictor 48 is, for example, available under the trademark AirLogic®.

Wound dressing 11 can preferably include sterile foam laminate dressing 100, semi-permeable transparent adhesive cover 52 which can be a plastic sheet of polyurethane material such as that sold under the trademark DeRoyal® or Avery Denison®.

The semi-permeable adhesive cover 52 can then be formed to include an inlet port 56 and a suction port 54. Substrate 100 is configured to distribute vacuum pressure evenly throughout the entire wound bed and has mechanical properties suitable for promoting the formation of granular tissue and approximating the wound margins.

In addition, when vacuum is applied to dressing 11, substrate 100 creates micro- and macro-strain at the cellular level of the wound stimulating the production of various growth factors and other cytokines, and promoting cell proliferation. Dressing 11 is fluidically associated with canister 22 through single-lumen tube 44. The vacuum pressure in a cavity formed by substrate 100 of dressing 11 is largely the same as the vacuum pressure inside canister 22 minus the weight of any standing fluid inside tubing 44.

A fluid vessel 60, which can be a standard IV bag, contains medicinal fluids such as aqueous topical antibiotics, analgesics, physiologic bleaches, or isotonic saline. Fluid vessel 60 is removably connected to dressing 11 through port 56 and single-lumen tube 62.

An optional flow control device 64 can be placed in-line with tubing 62 to permit accurate regulation of the fluid flow from vessel 60 to dressing 11. In normal operation, continuous wound site irrigation is provided as treatment fluids move from vessel 60 through dressing 11 and into collection canister 22. This continuous irrigation keeps the wound clean and helps to manage infection. In addition, effluent produced at the wound site and collected by substrate 52 will be removed to canister 22 when the system is under vacuum.

The device 10 is particularly well suited for providing therapeutic wound irrigation and vacuum drainage and provides for a self-contained plastic housing configured to be worn around the waist or carried in a pouch over the shoulder for patients who are ambulatory, and hung from the footboard or headboard of a bed for patients who are non-ambulatory. Membrane keypad and display 16 is provided to enable the adjustment of therapeutic parameters and to turn the unit on and off.

Depressing the power button on membrane switch 16 will turn the power to device 10 on/off. While it is contemplated that the membrane switch 16 be equipped with keys to adjust therapeutic pressure up and down, the microcontroller 14 can preferably be equipped to control the pressure in accordance with sensed pressure and condition to maintain pressure in an operable range between −70 mmHg and −150 mmHg with a working range of between 0 and −500 mmHg, for example. Although these pressure settings are provided by way of example, they are not intended to be limiting because other pressures can be utilized for wound-type specific applications. The membrane 16 can also be equipped with LED 17 to indicate a leak alarm and/or LED 19 indicates a full-canister alarm. When either alarm condition is detected, these LEDs will light in conjunction with an audible chime which is also included in the device 10.

Housing 12 can incorporate a compartment configured in such a way as to receive and store a standard IV bag 60 or can be externally coupled to thereto. IV bag 60 may contain an aqueous topical wound treatment fluid that is utilized by the device 60 to provide continuous irrigation. A belt clip can provided for attaching to a patient's belt and an optional waist strap or shoulder strap is provided for patients who do not or cannot wear belts.

Canister 22 is provided for exudate collection and can preferably be configured as currently known in the field with a vacuum-sealing means and associated fluid barrier 26, vacuum sensor port 43 and associated protective hydrophobic filter, contact-clear translucent body, clear graduated measurement window, locking means and tubing connection means. Collection canister 22 typically has a volume less than 1000 ml to prevent accidental exsanguination of a patient if hemostasis is not achieved in the wound. Fluid barriers 26 can be, for example, those sold under the trademark MicroPore® or GoreTex® and ensure the contents of canister 22 do not inadvertently ingress into pumps 18, 20 of housing 12 and subsequently cause contamination of thereof.

Pressure sensor 42 enables microcontroller 14 to measure the pressure within the canister 22 as a proxy for the therapeutic vacuum pressure under the dressing 11.

Optionally, tubing 62 can be multilumen tubing providing one conduit for the irrigation fluid to travel to dressing 11 and another conduit for the vacuum drainage. Thus, IV bag 60, tubing 62, dressing 11 and canister 22 provide a closed fluid pathway. In this embodiment, canister 22 would be single-use disposable and may be filled with a solidifying agent 23 to enable the contents to solidify prior to disposal. Solidifying agents are available, for example, under the trademark DeRoyal® and Isolyzer®. The solidifying agents prevent fluid from sloshing around inside the canister particularly when the patient is mobile, such as would be the case if the patient were travelling in a motor vehicle. In addition, solidifying agents are available with antimicrobials that can destroy pathogens and help prevent aerosolization of bacteria.

At the termination of optional multilumen tubing 62, there can be provided a self-adhesive dressing connector 57 for attaching tubing 62 to semi-permeable transparent adhesive cover 52 to provide a substantially air-tight seal. Dressing connector 57 can have an annular pressure-sensitive adhesive ring with a release liner that is removed prior to application. Port 56 can be formed as a hole cut in a semi-permeable transparent adhesive cover 52 and dressing connector 57 would be positioned in alignment with said hole. This enables irrigation fluid to both enter and leave the dressing through a single port. In an alternative embodiment, tube 62 can bifurcate at the terminus and connect to two dressing connectors 57 which allow the irrigation port to be physically separated from the vacuum drainage port thus forcing irrigation fluid to flow through the entire length of the dressing if it is so desired. Similarly, port 54 and connector 55 can be provided to connect optional multilumen tubing 44 to dressing 11. In this arrangement, the second lumen may be used to directly measure the pressure in dressing 11.

Fluid vessel 60 can be of the type which includes a self-sealing needle port situated on the superior aspect of the vessel 60 and a regulated drip port situated on the inferior aspect of the vessel. The needle port permits the introduction of a hypodermic needle for the administration of aqueous topical wound treatment fluids. These aqueous topical fluids can include a topical anesthetic such as Lidocaine, antibiotics such as Bacitracin or Sulfamide-Acetate; physiologic bleach such as Chlorpactin or Dakins solution; and antiseptics such as Lavasept or Octenisept. Regulated drip port permits fluid within vessel 60 to egress slowly and continuously into porous substrate 100 whereupon the therapeutic benefits can be imparted to the wound site. Single-lumen drainage tube 44 provides enough vacuum to keep the dressing 11 at sub-atmospheric pressure and to remove fluids, which include the irrigation fluid and wound exudates. With this modification, the need for an external fluid vessel and associated tubing and connectors can be eliminated making the dressing more user friendly for patient and clinician alike.

In typical clinical use of this alternate embodiment, dressing 11 is applied to the wound site by first cutting porous substrate 100 to fit the margins of the wound. Next, a semi-permeable transparent adhesive cover 52 is attached and sealed over the dressing and periwound. A hole approximately ⅜" diameter can be made in a semi-permeable transparent adhesive cover 52 central to porous substrate 100. Fluid vessel 60 is attached by adhesive annular ring 57 with port 56 aligned with the hole previously cut in a semi-permeable transparent adhesive cover 52. Once the fluid vessel 60 is hermitically sealed to the semi-permeable transparent adhesive cover 52, a properly prepared hypodermic needle is inserted in self-sealing needle port and fluid vessel 60 subsequently filled with the desired aqueous topical wound treatment solution.

For the majority of applications, the technique for providing therapeutic wound irrigation and vacuum drainage is illustrated. The single lumen drainage tube 44 is provided for the application of vacuum and removal of fluids from the wound site. Fluid vessel 60 can be situated outside and superior to semi-permeable substrate 100. An annular adhesive ring 57 is provided on port 56 for attachment of single-lumen irrigation tubing 62 to a semi-permeable transparent adhesive cover 52. Similarly, a needle port permits the introduction of a hypodermic needle for the administration of aqueous topical wound treatment fluids as described above, for example, a caregiver may want to add a topical antibiotic to a bag of isotonic saline. Adjustable optional flow control device 64 permits fluid within vessel 60 to egress slowly and continuously into porous substrate 52 through hole 56 in a semi-permeable transparent adhesive cover 52 whereupon the therapeutic benefits can be imparted to the wound site. Single-lumen drainage tube 44 provides enough vacuum to keep the dressing 11 at sub-atmospheric pressure and to remove fluids which include the irrigation fluid and wound exudates.

Because of the potential chemical interactions between the various materials used in the construction of dressing 11, attention must be paid to the types of aqueous topical wound fluids used to ensure compatibility.

The above described embodiments are set forth by way of example and are not limiting. It will be readily apparent that obvious modifications, derivations and variations can be made to the embodiments. For example, the vacuum pumps described having either a diaphragm or piston-type could also be one of a syringe based system, bellows, or even an oscillating linear pump. Accordingly, the claims appended hereto should be read in their full scope including any such modifications, derivations and variations.

What is claimed is:

1. A foam laminate dressing comprising:
   A) a foam laminate consisting of:
   a first distinct hydrophobic reticulated foam layer; and
   an underlying second distinct hydrophilic layer mechanically interlocked with said first distinct hydrophobic reticulated foam layer and of substantially same length and width as said first distinct hydrophobic reticulated foam layer,
   wherein the foam laminate is formed by a process comprising:
   a) providing the first distinct hydrophobic reticulated foam layer immediately disposed the second distinct hydrophilic layer, and
   b) after a), curing the first distinct hydrophobic reticulated foam layer and the second distinct hydrophilic layer to provide mechanical interlocking between the first distinct hydrophobic reticulated foam layer and the second distinct hydrophilic layer;
   B) a hermetic sealing layer connected adjacent to and covering said first distinct hydrophobic reticulated foam layer and of a size greater than said first distinct hydrophobic reticulated foam layer;
   wherein the hermetic sealing layer is configured to attach over the foam laminate and seal a periwound area; and
   C) a negative pressure device operably connected to a port on said hermetic sealing layer.

2. The foam laminate dressing of claim 1, wherein said foam laminate is spiral cut with perforations to enable said foam laminate to be easily torn to accommodate a particular wound size.

3. The foam laminate dressing of claim 1, wherein at least one layer is a polyurethane.

4. The foam laminate dressing of claim 3, wherein the second distinct hydrophilic layer is a polyurethane.

5. The foam laminate dressing of claim 3, wherein the first distinct hydrophobic reticulated foam layer is a polyurethane.

6. The foam laminate dressing of claim 1, wherein the first and second layers are polyurethanes.

7. A foam laminate dressing comprising:
   A) foam laminate consisting of:
   a first distinct hydrophobic reticulated polyurethane foam layer; and
   an underlying second distinct hydrophilic layer mechanically interlocked with said first distinct hydrophobic reticulated polyurethane foam layer and of substantially same length and width as said first distinct hydrophobic reticulated polyurethane foam layer, B) a hermetic sealing layer connected adjacent to and covering said first distinct hydrophobic reticulated polyurethane foam layer and of a size greater than said first distinct hydrophobic reticulated polyurethane foam layer;

wherein the hermetic sealing layer is configured to attach over the foam laminate and seal a periwound area, and C) a negative pressure device operably connected to a port on said hermetic sealing layer, wherein the foam laminate is formed by a process comprising:

a) providing the first distinct hydrophobic reticulated foam layer immediately disposed the second distinct hydrophilic layer, and b) after a), curing the first distinct hydrophobic reticulated foam layer and the second distinct hydrophilic layer to provide mechanical interlocking between the first distinct hydrophobic reticulated foam layer and the second distinct hydrophilic layer.

8. The foam laminate dressing of claim 7, wherein the second distinct hydrophilic layer is a polyurethane.

9. The foam laminate dressing of claim 7, wherein the foam laminate is spiral cut with perforations to enable said foam laminate to be easily torn to accommodate a particular wound size.

10. A foam laminate dressing comprising:

A) foam laminate consisting of:

a first distinct hydrophobic reticulated polyurethane foam layer;

an underlying second distinct hydrophilic polyurethane layer mechanically interlocked with said first distinct hydrophobic reticulated polyurethane foam layer and of substantially same length and width as said first distinct hydrophobic reticulated polyurethane foam layer, wherein the foam laminate is spiral cut with perforations to enable said foam laminate to be easily torn to accommodate a particular wound size, and wherein the foam laminate is formed by a process comprising:

a) providing the first distinct hydrophobic reticulated foam layer immediately disposed the second distinct hydrophilic layer, and b) after a), curing the first distinct hydrophobic reticulated foam layer and the second distinct hydrophilic layer to provide mechanical interlocking between the first distinct hydrophobic reticulated foam layer and the second distinct hydrophilic layer;

B) a hermetic sealing layer connected adjacent to and covering said first distinct hydrophobic reticulated polyurethane foam layer and of a size greater than said first distinct hydrophobic reticulated polyurethane foam layer;

wherein the hermetic sealing layer is configured to attach over the foam laminate and seal a periwound area; and C) a negative pressure device operably connected to a port on said hermetic sealing layer.

* * * * *